US008801680B2

(12) United States Patent
Wong et al.

(10) Patent No.: US 8,801,680 B2
(45) Date of Patent: Aug. 12, 2014

(54) ANGLED RETRACTING SHEATH FOR SAFETY NEEDLE

(71) Applicants: Andrew Wong, East Hanover, NJ (US); Matthew Zachek, Ridgewood, NJ (US)

(72) Inventors: Andrew Wong, East Hanover, NJ (US); Matthew Zachek, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/793,831

(22) Filed: Mar. 11, 2013

(65) Prior Publication Data

US 2013/0261565 A1    Oct. 3, 2013

Related U.S. Application Data

(60) Provisional application No. 61/610,576, filed on Mar. 14, 2012.

(51) Int. Cl.
*A61M 5/00* (2006.01)

(52) U.S. Cl.
USPC .......................................................... 604/263

(58) Field of Classification Search
USPC ................................................. 604/117, 263
See application file for complete search history.

(56) References Cited

U.S. PATENT DOCUMENTS

| | | | | |
|---|---|---|---|---|
| 4,775,369 A | * | 10/1988 | Schwartz | 604/263 |
| 4,911,693 A | * | 3/1990 | Paris | 604/192 |
| 5,088,986 A | * | 2/1992 | Nusbaum | 604/195 |
| 5,147,327 A | * | 9/1992 | Johnson | 604/198 |
| 5,211,628 A | * | 5/1993 | Marshall | 604/110 |
| 5,242,418 A | * | 9/1993 | Weinstein | 604/192 |
| 5,256,152 A | | 10/1993 | Marks | |
| 5,472,430 A | * | 12/1995 | Vaillancourt et al. | 604/198 |
| 5,478,328 A | * | 12/1995 | Silverman et al. | 604/272 |
| 5,487,733 A | * | 1/1996 | Caizza et al. | 604/110 |
| 5,512,050 A | * | 4/1996 | Caizza et al. | 604/263 |
| 5,591,138 A | * | 1/1997 | Vaillancourt | 604/263 |

(Continued)

FOREIGN PATENT DOCUMENTS

| | | |
|---|---|---|
| EP | 1066848 | 1/2001 |
| WO | WO-02076526 | 10/2002 |

(Continued)

OTHER PUBLICATIONS

PCT International Search Report and Written Opinion in PCT/US2013/031191, mailed Feb. 21, 2014, 17 pages.

*Primary Examiner* — Nicholas Lucchesi
*Assistant Examiner* — Diva K Chander
(74) *Attorney, Agent, or Firm* — Servilla Whitney LLC (57) ABSTRACT

A safety needle device having a housing, a retractable sheath, and a needle cannula. The retractable sheath includes a tubular portion that is slideably mounted about a portion of the housing to completely or partially encase the length of the cannula. The retractable sheath includes a sheath bevel at the distal end having a blunted or angled tip. The angled tip being configured to suitable injection angles and may be fixed or rotatable. The sheath bevel may include a skin-engaging contact surface at the distal end. The needle may be connected to a needle hub at the proximal end of the housing and includes a needle bevel at the distal end. The sheath bevel and needle bevel may be offset from each other. A safety needle device having a retractable sheath having a graduated injection depth gauge to indicate needle penetration is also disclosed.

19 Claims, 5 Drawing Sheets

(56) References Cited

U.S. PATENT DOCUMENTS

| | | | |
|---|---|---|---|
| 5,895,395 A * | 4/1999 | Yeung | 606/144 |
| 6,530,933 B1 * | 3/2003 | Yeung et al. | 606/151 |
| 7,744,565 B2 | 6/2010 | Heiniger et al. | |
| 2004/0102740 A1 | 5/2004 | Meloul | |
| 2006/0030884 A1 * | 2/2006 | Yeung et al. | 606/232 |
| 2013/0261565 A1 * | 10/2013 | Wong et al. | 604/263 |

FOREIGN PATENT DOCUMENTS

| | | |
|---|---|---|
| WO | WO-2004004803 | 1/2004 |
| WO | WO-2008131440 | 10/2008 |
| WO | WO-2011112916 | 9/2011 |

* cited by examiner

ANGLED RETRACTING SHEATH FOR SAFETY NEEDLE

CROSS-REFERENCE TO RELATED APPLICATIONS

This application claims priority under 35 U.S.C. §119(e) to U.S. Provisional Application No. 61/610,576, filed Mar. 14, 2012, the disclosures of which are incorporated herein by reference in their entirety.

TECHNICAL FIELD

The subject invention relates generally to a safety needle device, and more particularly to a safety needle device having a housing, a retractable sheath, and a needle cannula. The retractable sheath having a tubular portion that is slideably mounted about a portion of the housing to completely or partially encase the length of the cannula. The retractable sheath also having a sheath bevel at the distal end. The sheath bevel having a blunted or angled tip. The angled tip being configured to suitable injection angles and may be fixed or rotatable. The sheath bevel may have a skin-engaging contact surface at the distal end. The needle may be connected to a needle hub at the proximal end of the housing and includes a needle bevel at the distal end. The sheath bevel and needle bevel may be offset from each other. A safety needle device having a retractable sheath having a graduated injection depth gauge to indicate needle penetration is also disclosed.

BACKGROUND

Needle devices are used throughout the medical industry for the injection and withdrawal of a wide variety of fluids and solutions into and from the human body. Because of the numerous potential hazards associated with the handling and manipulation of bodily fluids, and particularly blood, there are a number of known safety features that are frequently incorporated into various types of needle devices to protect the practitioner from accidental exposure to the needle.

Prior retracting sheath safety needle devices have been developed to include a blunt tip suited for injection perpendicular to the injection site. While a blunt tip may be ideal for most intramuscular injections, the administration of other injection techniques, such as intradermal or subcutaneous, may require different injection angles. For example, shallow injection angles are difficult or impossible with existing safety needle devices.

Prior retracting sheath safety needle devices have been developed to include a single-use cover assembly that obscures a substantial majority or an entirety of an injection needle from view before, during, and after an injection procedure. However, many injection procedures require that the practitioner know precisely the depth to which the needle is inserted in the patient's tissue to be sure that medication is delivered to an appropriate location. Prior retracting sheath safety needle devices do not have depth gauges so that injection depth can be quickly and easily determined.

There is a need in the art to provide a safety needle device having a sheath tip configured to various different injection angles to facilitate the administration of injection techniques, such as intradermal and subcutaneous, which may require shallow injection angles.

There is a also need in the art to provide a safety needle device having a depth gauge feature that is capable of quickly and easily determining the injection depth, which is especially useful for certain types of injections, such as intramuscular and subcutaneous.

SUMMARY

The present invention is directed to a safety needle device including a housing having a proximal end and a distal end having an opening. The safety needle device also includes a retractable sheath disposed and movable in the opening and surrounding a needle. The needle may be connected to a needle hub at the proximal end of the housing and having a blunted tip or beveled tip at the distal end. In one or more embodiments, the proximal end of the housing may be connectable to a luer connection or other fluid connector, or integrated into a device such as a syringe. The retractable sheath may include a sheath bevel at the distal end. The sheath bevel and needle bevel being offset from each other. In one embodiment, the sheath bevel and needle bevel may be offset by 180 degrees.

In one or more embodiments of the present invention, the sheath bevel includes a section of skin-engaging contact surfaces. The section of skin-engaging contact surfaces holds skin taut prior to an injection and may include a friction enhancing material.

In one or more embodiments of the present invention, the sheath bevel includes at least one injection angle guide configured in the range between 10 to 90 degrees. In one or more embodiments, the injection angle guide may be configured in the range between 5 to 50 degrees. In another embodiment, the injection angle guide is configured as a blunted tip.

In yet another embodiment, the sheath bevel includes at least two injection angle guides wherein a first injection angle guide is configured in the range between 10 to 90 degrees and a second injection angle guide is configured to be larger than the first angle and is in the range between 10 to 90 degrees. In one or more embodiments, the first injection angle guide is configured as a blunted tip. In one or more embodiments, the second injection angle guide is configured as a blunted tip.

In one or more embodiments, the injection angle guide may be fixed or rotatable to adjust the needle bevel angle relative to an injection site.

In one or more embodiments, the sheath bevel may have a frusto-conically shaped tip.

The frusto-conically shaped tip may be transparent, and may be comprised of a different material and/or may includes a thin transparent overmold. The tip and/or overmold may be made of a material having a high coefficient of friction with skin.

In one or more embodiments, the sheath bevel may have a curved tip. The curved tip may include a high friction contact surface.

In one or more embodiments, the sheath bevel may have a blunted tip including an axial projection directed in the distal direction. The axial projection may further include a nub made of a material having a high coefficient of friction with skin.

The present invention is also directed to a safety needle device including a housing having a proximal end and a distal end having an opening. In one or more embodiments, the proximal end of the housing may be connectable to a luer connection or other fluid connector, or integrated into a device such as a syringe.

The safety needle device also includes a retractable sheath disposed and movable in the opening and surrounding a needle. The retractable sheath may include a graduated injection depth gauge to indicate needle penetration and a sheath bevel at the distal end. The needle may be connected to a needle hub at the proximal end of the housing and may have a needle bevel at the distal end. The sheath bevel and needle bevel may be offset from each other.

In one or more embodiments, the graduated injection depth gauge may be printed onto an outer surface of the retractable sheath. In another embodiment, the graduated injection depth gauge may be engraved, etched, embossed, debossed by molding or formed onto an outer surface of the retractable sheath.

In one or more embodiments, the graduated injection depth gauge may be scaled to correlate to needle length or injection angles. The needle penetration depth may be read from the intersection of the scale and the hub.

The safety needle device may further include a visual indicator for reading the graduated injection depth gauge, including a magnified window, arrow, line or other feature or visible mark printed or formed on the retractable sheath.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

In this disclosure, a convention is followed wherein the distal end of the device is the end closest to a patient and the proximal end of the device is the end away from the patient and closest to a practitioner.

Figure 1:
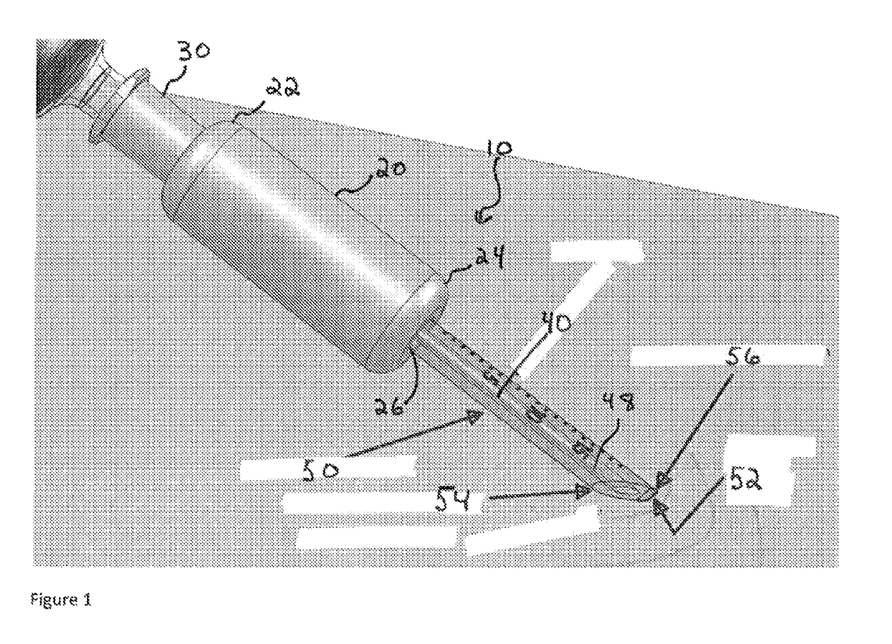
FIG. 1 is a perspective view of the safety needle device prior to injection in skin.

FIG. 1 illustrates an exemplary safety needle device 10 according to the present invention. Generally speaking, safety needle device 10 is comprised of a needle 40, a housing 20, and a retractable sheath 50. Housing 20 includes a proximal end 22 and a distal end 24 having an opening 26. In one or more embodiments, the proximal end of the housing may be connectable to a luer connection 30 or other fluid connector. Retractable sheath 50 is slidably mounted and movable in the opening 26 to slidably accommodate and encase needle 40 projecting axially from housing 20. The term "retractable sheath" is intended to include any sort of tubular member. The retractable sheath 50 is dimensioned to be compatible with the size and type of needle 40 as will be appreciated by those skilled in the art. The housing 20 may include a housing body portion with an internal hollow region (not shown) in which the retractable sheath 50 may move in the proximal direction. Needle 40 may be connected to a needle hub (not shown) disposed at the proximal end 22 of the housing 20 and having a blunted tip or beveled tip at the distal end. The needle is disposed in the needle hub in a manner as would be well understood in the art and which forms no part of the invention. The needle hub may be integrally formed with housing body portion. The needle 40 extends from the needle hub disposed in the housing 20 to a needle tip and is completely received within the retractable sheath 50 when the retractable sheath 50 is in a distal position. The needle tip is exposed from the retractable sheath 50 when the retractable sheath 50 is in a proximal position. The retractable sheath 50 may include a sheath bevel 54 at the distal end. The sheath bevel 54 and needle bevel 48 being offset from each other. In one embodiment, the sheath bevel 54 and needle bevel 48 may be offset by 180 degrees.

Figure 2:
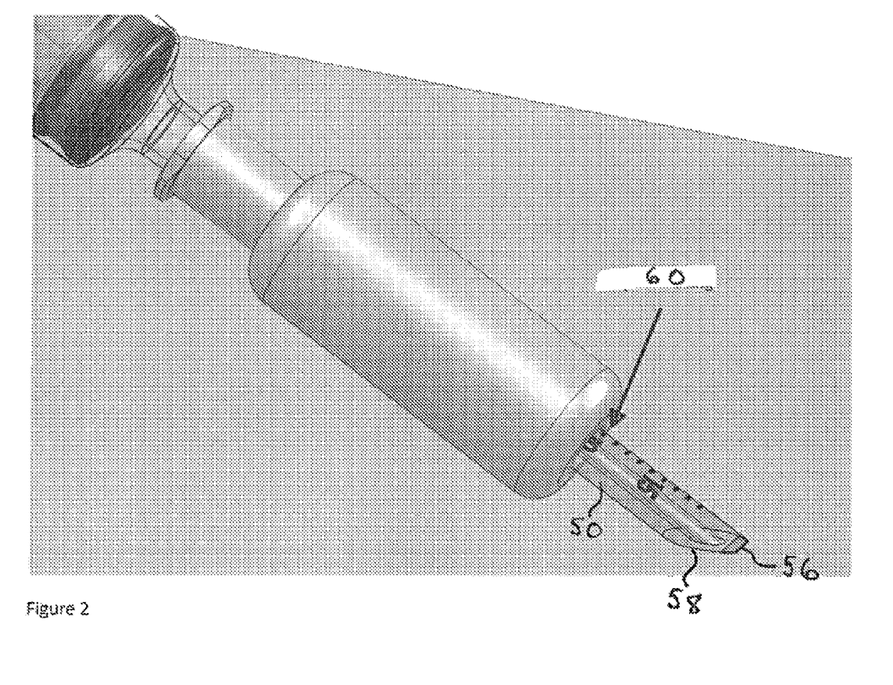
FIG. 2 is a perspective view of the safety needle device after injection into skin.

As illustrated in several of the drawings, most notably FIG. 2, retractable sheath 50 is generally comprised of a tubular portion and is retractably slidable along the length of the needle 40 such that at least a substantial portion of needle 40 is exposed when the sheath 50 is in its retracted position. As shown in FIG. 1, the length of needle 40 extending outwardly from the needle hub in a distal direction is partially or completely encased when retractable sheath 50 is in its non-retracted position.

Upon administration of the injection, the retractable sheath 50 moves from a distal to proximal position and the needle tip is exposed so that the needle tip may penetrate the injection site. Upon continued application of force by pressing sheath 50 against the skin at the location where it is desired to insert needle 40, sheath 50 retracts into housing 20 allowing the injection site to be penetrated by the needle tip. When the retractable sheath 50 reaches a fully retracted position (in the proximal most position), the needle reaches a fully extended position, in which the needle tip achieves its maximum penetration of the injection site. Upon completion of an injection, the practitioner need only withdraw the needle so as to cause the retractable sheath 50 to resiliently return toward the fully extended condition to once again be repositioned to encase needle 40. In one or more embodiments of the present invention, the retractable sheath is connected to the proximal end of the housing by a spring mechanism that acts to resiliently return the retractable sheath toward the fully extended condition.

Retracting sheath 50 may include a bevel formed or cut into the tip at angles ideal for specific injection procedures. For example, for intradermal injections the ideal injection angle may be 10-15 degrees therefore, in one or more embodiments of the present invention, the bevel tip would be 10-15 degrees to guide the user at this angle. In one or more embodiments of the present invention, the sheath bevel 54 includes at least one injection angle guide configured in the range between 10 to 90 degrees. In one or more embodiments, the injection angle guide 58 may be configured in the range between 5 to 50 degrees. In another embodiment, the extreme tip of the injection angle guide is configured as a blunted tip 52 so that perpendicular injections continue to be comfortable to a patient.

Figure 3:
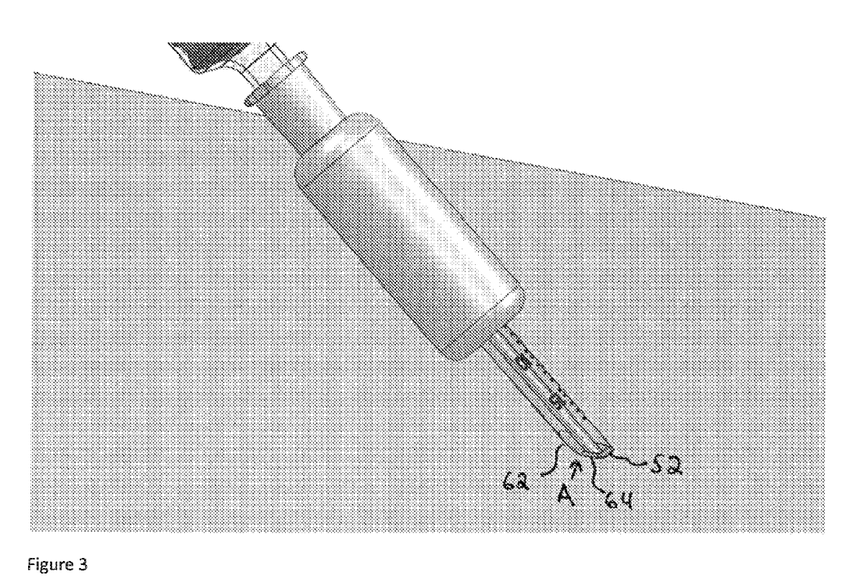
FIG. 3 is a perspective view of the safety needle device having two bevel guides in accordance with an alternative embodiment of the present invention.

In yet another embodiment, the sheath bevel 54 includes at least two injection angle guides wherein a first injection angle guide is configured in the range between 10 to 90 degrees and a second injection angle guide is configured to be larger than the first angle and is in the range between 10 to 90 degrees. In one or more embodiments, the first injection angle guide may be configured as a blunted tip. In one or more embodiments, the second injection angle guide may be configured as a blunted tip. In one or more embodiments, a third or more injection angle guide may be configured as a blunted tip. A multi-beveled sheath point may be formed through a plurality of individual bevels that together define a beveled face about the periphery of distal end of the retractable sheath. In one embodiment, the multi-beveled point is characterized by a primary bevel 62; a secondary bevel 64, and a blunted tip 52. The secondary bevel 64 is formed on opposite sides of primary bevel 62. Primary bevel 62 and secondary bevels 64 meet at an intersection "A" shown in FIG. 3 demarcating the respective planes at which the primary bevel and secondary bevels are formed. This would allow for almost all common injection techniques, with shallow, medium, and perpendicular injection angles.

Figure 4:
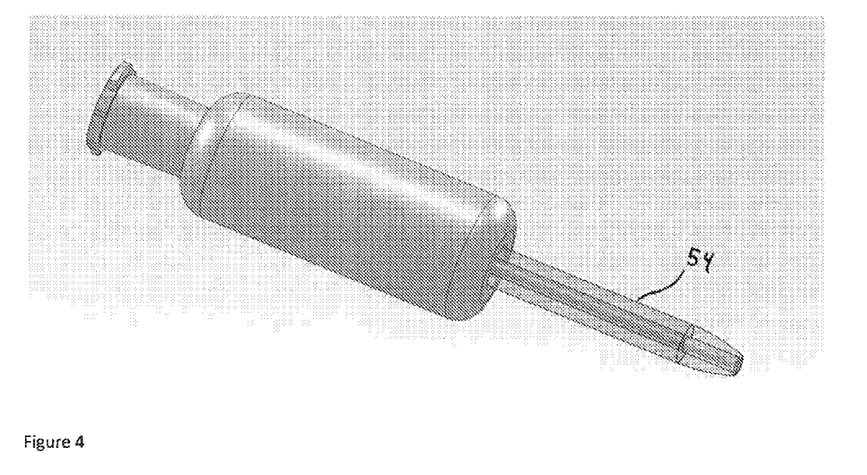
FIG. 4 is a perspective view of the safety needle device having two bevel guides in accordance with an alternative embodiment of the present invention.
Figure 5:
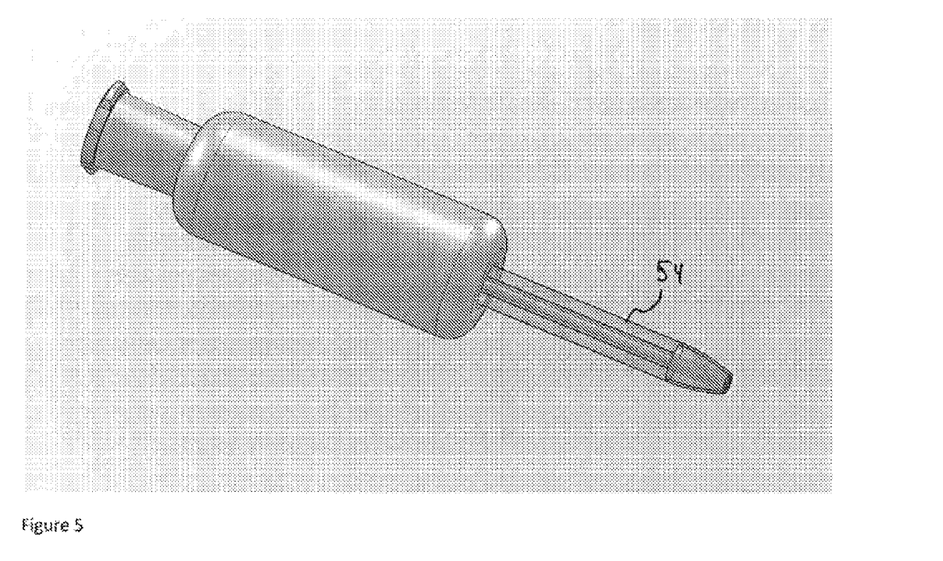
FIG. 5 is a perspective view of the safety needle device having two bevel guides in accordance with an alternative embodiment of the present invention.
Figure 6:
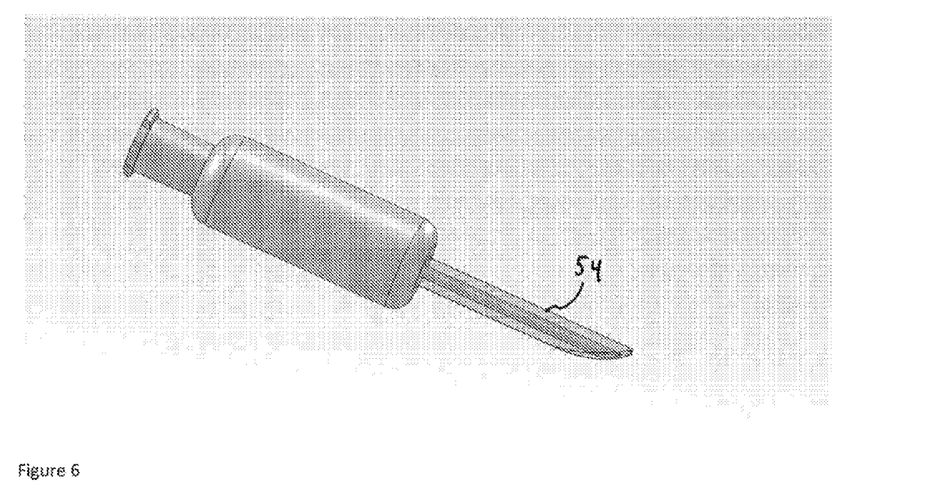
FIG. 6 is a perspective view of the safety needle device having two bevel guides in accordance with an alternative embodiment of the present invention.
Figure 7:
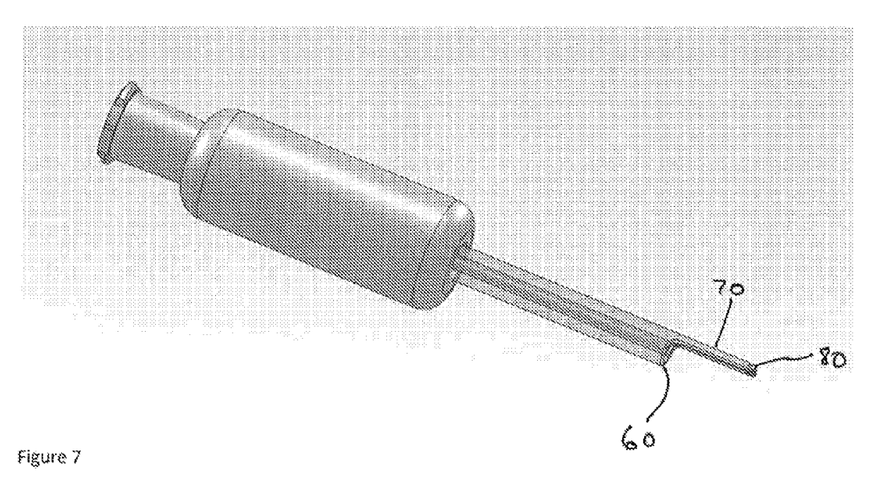
FIG. 7 is a perspective view of the safety needle device having two bevel guides in accordance with an alternative embodiment of the present invention.

As shown in FIGS. 4-7, it is envisioned that the sheath bevel 54 in one or more embodiments is configured to allow for continuously variable injection angles. As shown in FIGS. 4 and 5, the bevel tip may be configured in a frusto-conical shape to allow for continuously variable injection angles. As shown in FIG. 4, the sheath bevel 54 may also include a rubbery transparent tip. The sheath bevel 54 may also include a thin, preferably transparent overmold, as shown in FIG. 5. The overmold can be made of any resilient, flexible material with adequate coefficient of friction with the skin including, but not limited to, rubber. FIG. 6 shows the sheath bevel having a curved contact surface. The curved tip of the sheath bevel may also include a grippy high friction contact surface. The material of construction of the high friction contact surface can be any resilient, flexible material with adequate coefficient of friction with the skin. Suitable materials include substances such as latex rubber, butyl rubber, silicone, and the like. Alternately, additional materials may be omitted if contact surfaces have sufficient grip. FIG. 7 shows the sheath bevel having a blunted tip 60 including an axial projection 70 directed in the distal direction. The axial projection of the blunted tip may also include a nub 80. The material of construction of the nub on the axial projection can be any resilient, flexible material with adequate coefficient of friction with the skin. Suitable materials for the nub include substances such as latex rubber, butyl rubber, silicone, and the like. In this embodiment, the tip of 70 is the sole point of contact, allowing rotation about that point, and therefore a continuously variable injection angle.

In one or more embodiments, the injection angle guide may be fixed or rotatable to adjust the needle bevel angle relative to an injection site. It is believed that most, if not all, common injections are either "bevel up" or non-oriented with respect to bevel. In a preferred embodiment, the needle bevel 48 is oriented in an upward position relative to the injection angle guide and injection angle.

In certain types of injection technique, it is desirable to pull the patient's skin taut prior to administration of the injection. In one or more embodiments of the present invention, the sheath bevel 54 includes a section of skin-engaging contact surface 56 for increasing the friction between bevel tip and the patient's skin to hold the patient's skin taut prior to an injection. Upon contact with the skin of the patient, the skin-engaging contact surface frictionally or adhesively engages and exerts an outward or lateral force on the injection site so that the skin is held taut prior to needle tip puncturing the injection site. At the same time, needle tip may be extended until needle tip penetrates the skin at the injection site. The skin engaging contact surface is placed on the bevel tip of the sheath. In a preferred embodiment, the section of skin-engaging contact surface 56 is positioned at a distal end of the sheath bevel. The section of skin-engaging contact surface 56 may be comprised of a friction enhancing material. The material of construction of the skin-engaging contact surface can be any resilient, flexible material with adequate coefficient of friction with the skin. Suitable materials include polymeric substances such as latex rubber, butyl rubber, silicone, and the like. In a preferred embodiment, the skin-engaging contact surface works in combination with the spring force of the sheath to pull the patient's skin taut.

The needle 40 in accordance with the present invention can be formed from conventional materials such as steel or more preferably stainless steel. It will be realized by the skilled artisan that medical grade plastics, composites, ceramics, or like materials can be substituted. The bevels can be formed on the needle 40 by conventional processes such as by grinding.

The inside diameter of the open-ended retracting sheath 50 is selected so that it will fit closely over needle 40 yet will slide freely along the needle 40. The retracting sheath 50 may be made of any suitable material, but preferably of a polymer which is tough enough to protect needle 40 and may be easily sterilized. The material is preferably transparent or translucent so that the position of needle 40 within retracting sheath 50 can be visually verified. Sheath 50 is preferably made of a transparent material, so that a health care worker can see the progress of needle 40 as it is emerging from sheath 50 to make sure that it is positioned where desired for an injection.

In another embodiment, the present invention is also directed to a safety needle device 10 including a housing 20, having a proximal end 22 and a distal end 24 having an opening 26, and a retractable sheath 50 having a graduated injection depth gauge to indicate needle penetration. In one or more embodiments, the proximal end of the housing may be connectable to a luer connection 30 or other fluid connector. The retractable sheath 50 is disposed and movable in the opening 26 and surrounds a needle 40. The retractable sheath 50 includes a sheath bevel 54 at the distal end. The needle 40 may be connected to a needle hub at the proximal end 22 of the housing 20 and may have a needle bevel 48 at the distal end. The sheath bevel 54 and needle bevel 48 may be offset from each other.

As injection is performed and needle 40 is inserted into tissue, the retractable sheath 50 is pushed into housing 20. As shown in FIGS. 1 and 2, the depth of the needle 40 can be read from the gauge where in enters the hub in the shown embodiment.

In one or more embodiments, the graduated injection depth gauge may be printed onto an outer surface of the retractable sheath 50. In another embodiment, the graduated injection depth gauge may be engraved, etched, embossed, debossed by molding or formed onto an outer surface of the retractable sheath 50 to assist the practitioner in measuring the needle depth penetration.

The depth gauge scale in the shown embodiment would be unique for each needle length.

It is envisioned that different injection angles on the same device may require different scales. For example, in a perpendicular injection, the needle 40 would enter at a different depth relative to the scale than in a shallow angle. Therefore, it is contemplated that multiple scales may be required if accurate readings are to be taken at different injection angles.

In one or more embodiments, the graduated injection depth gauge may be scaled to correlate to needle length or injection angles. The needle penetration depth may be read from the intersection of the penetration depth markers appearing on the outside of the retractable sheath 50 and the distal end of the housing 24. The depth markers may be arranged so that when the needle 40 is in an initial position, for example, the retractable sheath 50 is in the distal- most position, the position of the needle point relative to the depth markers indicates, for example, the maximum penetration depth of needle tip.

The safety needle device 10 may further include a visual indicator for reading the graduated injection depth gauge, including a magnified readout window, arrow, line or other feature or visible mark printed or formed on the retractable sheath 50. Other visual markers may also be utilized, for example, symbols and words may be disposed on the retracting sheath 50.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A safety needle device comprising:
   a housing having a proximal end and a distal end having an opening;
   a retractable sheath disposed and movable in the opening and surrounding a needle;
   the needle connected to a needle hub at the proximal end of the housing and having a needle bevel at the distal end;
   the retractable sheath having a sheath bevel at the distal end, the sheath bevel includes a section of skin-engaging contact surfaces comprised of a friction enhancing material to hold skin taut prior to an injection, the sheath bevel and needle bevel being offset from each other.

2. The safety needle device of claim 1, wherein the sheath bevel and needle bevel are offset by 180 degrees.

3. The safety needle device of claim 1, wherein the sheath bevel comprises at least one injection angle guide configured in the range between 5 to 90 degrees.

4. The safety needle device of claim 3, wherein the at least one injection angle guide is configured as a blunted tip.

5. The safety needle device of claim 1, wherein the sheath bevel comprises at least two injection angle guides.

6. The safety needle device of claim 5, wherein a first injection angle guide is configured in the range between 10 to 90 degrees and a second injection angle guide is configured to be larger than the first injection angle and is in the range between 10 to 90 degrees.

7. The safety needle device of claim 6, wherein the second injection angle guide is configured as a blunted tip.

8. The safety needle device of claim 6, further comprising a third injection angle guide configured as a blunted tip.

9. The safety needle device of claim 3, wherein the at least one injection angle guide is rotatable to adjust the needle bevel angle relative to an injection site.

10. The safety needle device of claim 1, wherein the sheath bevel has a frusto-conically shaped tip.

11. The safety needle device of claim 1, wherein the sheath bevel has a curved tip having a high friction contact surface.

12. The safety needle device of claim 1, wherein the sheath bevel comprises a blunted tip having an axial projection directed in the distal direction.

13. The safety needle device of claim 12, wherein the axial projection further includes a nub made of a material having a high coefficient of friction with skin.

14. A safety needle device comprising:
   a housing having a proximal end and a distal end having an opening;
   a retractable sheath disposed and movable in the opening and surrounding a needle, the retractable sheath having a graduated injection depth gauge to indicate needle penetration depth and a sheath bevel at the distal end; and a
   the needle connected to a needle hub at the proximal end of the housing and having a needle bevel at the distal end, wherein the needle penetration depth can be read from the intersection of the scale and the hub.

15. The safety needle device of claim 14, wherein the sheath bevel and needle bevel are offset from each other.

16. The safety needle device of claim 14, wherein the graduated injection depth gauge is printed, engraved, etched, embossed, or debossed onto an outer surface of the retractable sheath.

17. The safety needle device of claim 14, wherein the graduated injection depth gauge is scaled to correlate to needle length or injection angles.

18. The safety needle device of claim 14, further comprising a visual indicator for reading the graduated injection depth gauge.

19. The safety needle device of claim 18, wherein the indicator is a magnified window.

* * * * *